United States Patent [19]

Lowe

[11] 4,407,070
[45] Oct. 4, 1983

[54] ANIMAL MEASURING APPARATUS

[76] Inventor: Henry E. Lowe, 21725 Allegheny St., Cassopolis, Mich. 49031

[21] Appl. No.: 273,204

[22] Filed: Jun. 12, 1981

[51] Int. Cl.³ .............................................. G01B 5/02
[52] U.S. Cl. .................................................. 33/169 R
[58] Field of Search ............... 33/169 R, 17 R, 17 A, 33/174 D, 483, 494; 49/370, 410, 411

[56] References Cited

U.S. PATENT DOCUMENTS

| | | | |
|---|---|---|---|
| 333,281 | 12/1885 | Chase | 49/370 |
| 689,361 | 12/1901 | Moe | 33/17 R |
| 1,832,248 | 11/1931 | Schrader | 350/288 |
| 2,324,334 | 7/1943 | Sutton | 33/169 R |
| 4,182,080 | 1/1980 | Naylor | 49/410 |

FOREIGN PATENT DOCUMENTS

| | | | |
|---|---|---|---|
| 770377 | 6/1934 | France | 33/2 R |
| 50711 | 4/1932 | Norway | 33/17 R |

Primary Examiner—Harry N. Haroian
Attorney, Agent, or Firm—Marmaduke A. Hobbs; Raymond W. Campbell

[57] ABSTRACT

An animal measuring apparatus for measuring various parts of the anatomy of an animal, in which a wall is provided with lines representing graduations of a scale useful in measuring the animal. The lines of the scale extend the width of the wall, permitting measurement of various parts of the animal without moving the animal or scale. The wall can be of two panels suspended on a track for lateral movement in a vertical position, and the animal can be positioned between the panels.

9 Claims, 4 Drawing Figures

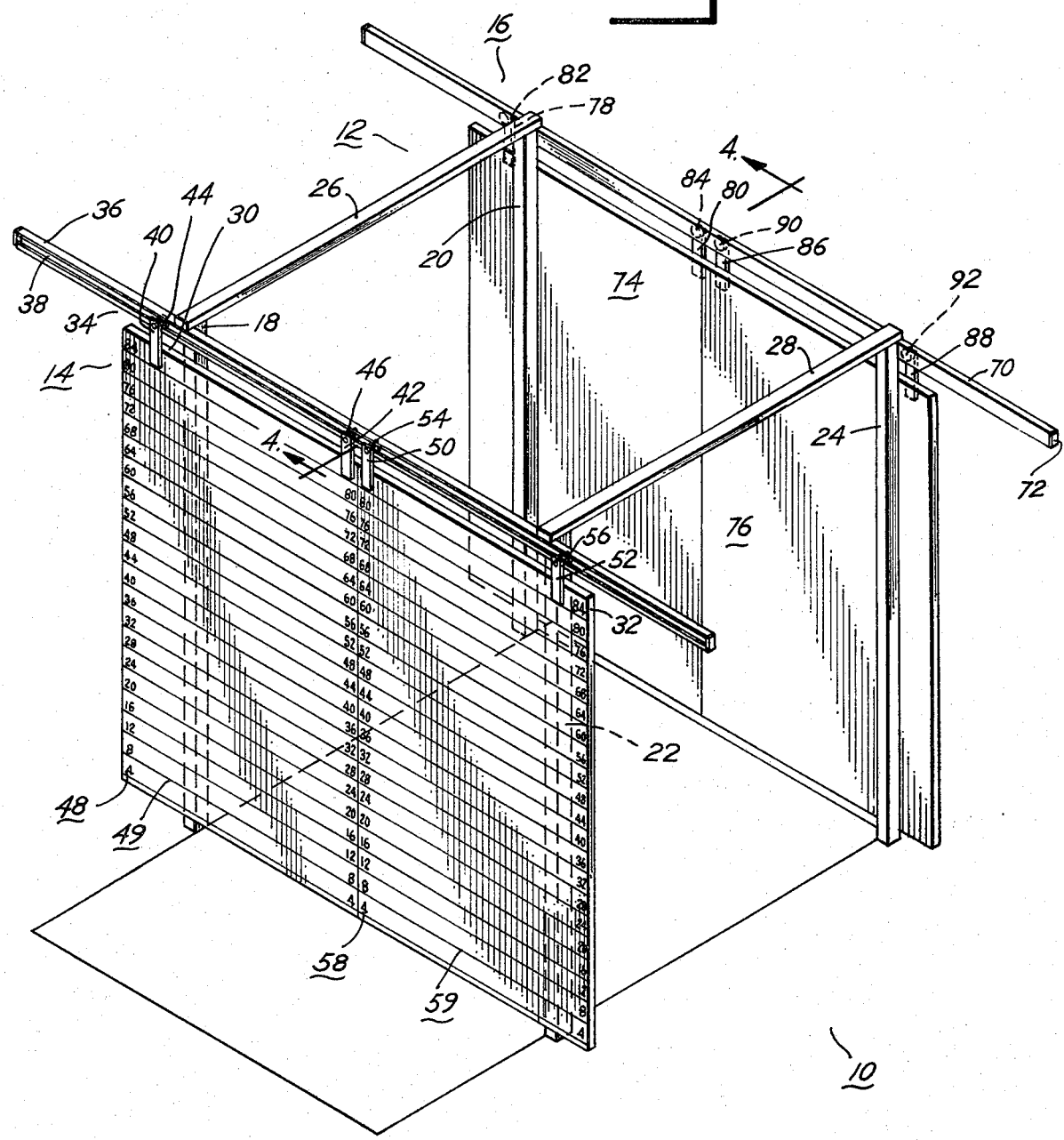

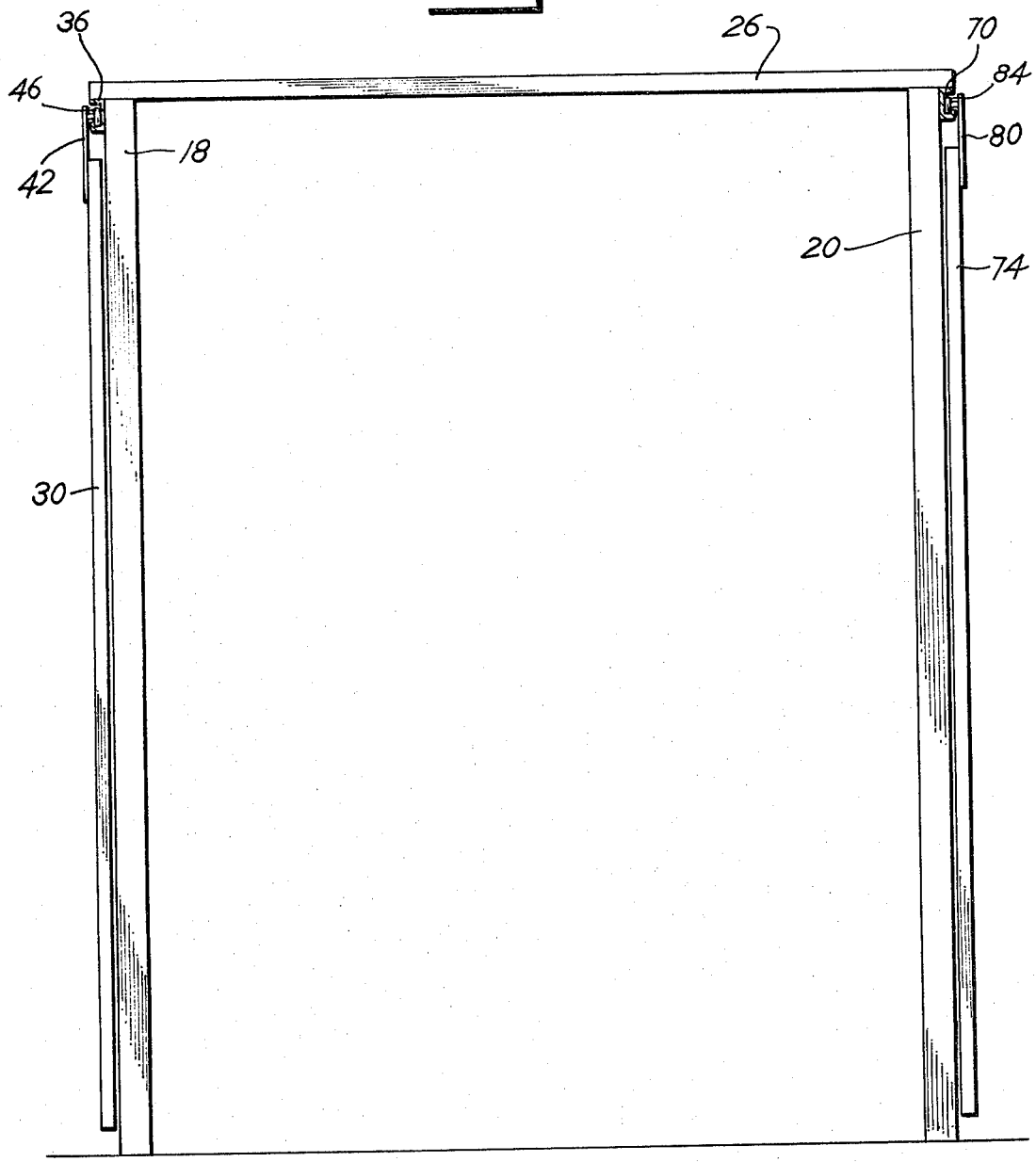

ANIMAL MEASURING APPARATUS

BACKGROUND OF THE INVENTION

In judging the quality and therefore the value of a horse, cow or other animal, size and physical appearance are important features. An experienced animal judge is able to estimate the size of an animal from casual observation, and, if he has sufficient practice, the estimate normally will be quite accurate with respect to the actual size of the animal. The height of horses has often been measured by the imprecise standard of "hands", the human hand being considered to be four inches wide, and the horse so measured is described as being so many hands high. When horses and other animals of high quality are being judged, whether for sale, awards competition or the like, precise measurements often are desirable. When a precise calculation of the size of an animal in inches or centimeters is required, a measuring tape or stick is often used, and two people are needed to make the measurement, one to hold the stick or tape and another to sight across the animal to the measuring scale. Even when the animal is precisely measured in inches or centimeters, its height may be expressed in the number of hands. The physical features of an animal are generally appraised by a personal evaluation on the part of the judge after carefully observing the animal. The judge will consider various different characteristics such as muscle structure, the prominence and over-prominence of certain features, and the symmetry of development of the animal. To properly evaluate the physical characteristics of the animal, the judge may often position himself at some distance from the animal, so that the overall appearance of the animal can be observed. If the judge desires, at the same time, to have a precise measurement of the size of the animal, he must leave his selected position from which the physical characteristics are appraised, approach the animal, measure it and then return to his judging position for a further appraisal of the same or other animals. When many animals are being judged in one session, the combined procedure of measuring and appraising can be a lengthy process.

Performance of the steps necessary to properly evaluate an animal requires an extensively developed knowledge of the desirable characteristics of the animal and the ability to appraise the individual physical characteristics in addition to the overall appearance of the animal. When the animal judging takes place in a barn, corral or other animal containment facility, it is often difficult to judge all of the animals on an equal basis and to properly evaluate the details of development in each animal. The background against which an animal is observed can effect the evaluation of the animal. For example, movement behind the animal can distract the judge, causing him to miss both beneficial and detrimental animal characteristics which would be recognizable only from concentrated observation of the animal. If each of the animals is not positioned in relatively the same location when the judging takes place, the background behind the animals can cause the animals to be judged on a less than equal basis. For example, if one animal is positioned in front of a stationary or a dark background and another animal is judged in front of a background of moving or light colored objects, the judge can be influenced by one or the other background during his personal evaluation of the animal. In some situations it becomes particularly difficult to properly evaluate the physical characteristics of an animal. If a horse or cow which has primarily dark hair is judged in front of a background which is dark, as for example trees or buildings, often it becomes difficult to follow the lines of the animal's body. Evaluating any animal, either light colored or dark colored, in front of a background of bright blue sky can be particularly difficult in that the judge is often forced to either squint or wear sunglasses, either of which can make the features of the animal more obscure, in which case muscle tone, bone projection and the like may be difficult to observe.

Yet another difficulty which arises in judging and evaluating animals is that to properly judge the animal it is desirable for the animal to remain calm and relatively stationary during much of the evaluation, so that the at-rest posture of the animal can be observed properly. Many times the animal will not be familiar with the judging environment and will be frightened by the judges and/or spectators. This can cause the animal to shift body weight from one leg to another, to prance slightly or to flinch, causing continuous flexion and relaxation of various muscle groups, making it relatively difficult to properly evaluate the animal. When the judge or animal handlers must approach the animal to make measurements as explained earlier, the animal frequently is frightened by their approach and may not stand still even for the measurement.

SUMMARY OF THE INVENTION

It is therefore one of the principal objects of the present invention to provide an animal measuring apparatus which enables one person to make a quick and accurate measurement of an animal, and which permits simultaneous measurement and comparison of the head, front legs and shoulders, back and hind quarters of an animal.

Another object of the present invention is to provide an animal measuring apparatus which provides a consistent background for judging all of the animals in a group of animals, and which helps to define the shape and lines of an animal so that an accurate observation of the physical characteristics of the animal can be made.

A further object of the present invention is to provide an animal measuring and judging apparatus which simplifies the comparative judging of body symmetry, which encourages the animal to remain calm throughout the judging procedure, and which permits a judge positioned some distance from the animal to make relatively precise measurements without approaching the animal.

These and other objects are accomplished in the present invention by providing a structure having a vertical surface in front of which the animals to be judged can be positioned, and a scale having graduated lines is provided on the surface for measuring an animal standing in front thereof. The lines of the scale preferably extend across the entire surface, forming the background behind the animal, and quick and accurate measurements can be made and compared. The lines also assist in judging characteristics such as the straightness of an animal's back. In the preferred structure the vertical surface has first and second panels suspended from a track assembly which permits the panels to be moved away from each other. An animal being judged can be positioned between the panels so that judging the symmetry of development in the animal is easier, faster and more convenient than in the past.

Additional objects and advantages of the present invention will become apparent from the detailed description and the accompanying drawings.

BRIEF DESCRIPTION OF THE DRAWINGS

FIG. 3 is a perspective view of an animal measuring apparatus embodying the present invention; and FIG. 4 is a cross sectional view of the apparatus shown in FIG. 3, taken on line 4—4 of the latter figure.

DETAILED DESCRIPTION OF THE PREFERRED EMBODIMENT

Referring now more specifically to the drawings, and to FIG. 3 in particular, numeral 10 designates an animal measuring apparatus embodying the present invention which can be used for measuring an animal and for providing a suitable background for judging various types of animals including horses, cows and the like. Reference hereinafter shall be made primarily to the judging of horses; however, it should be understood that the apparatus is equally advantageous when used for judging other animals. Depending on the type of animals for which the apparatus will be used, the overall size of the apparatus may vary substantially; however, the basic characteristics thereof will remain the same.

Figure 1:
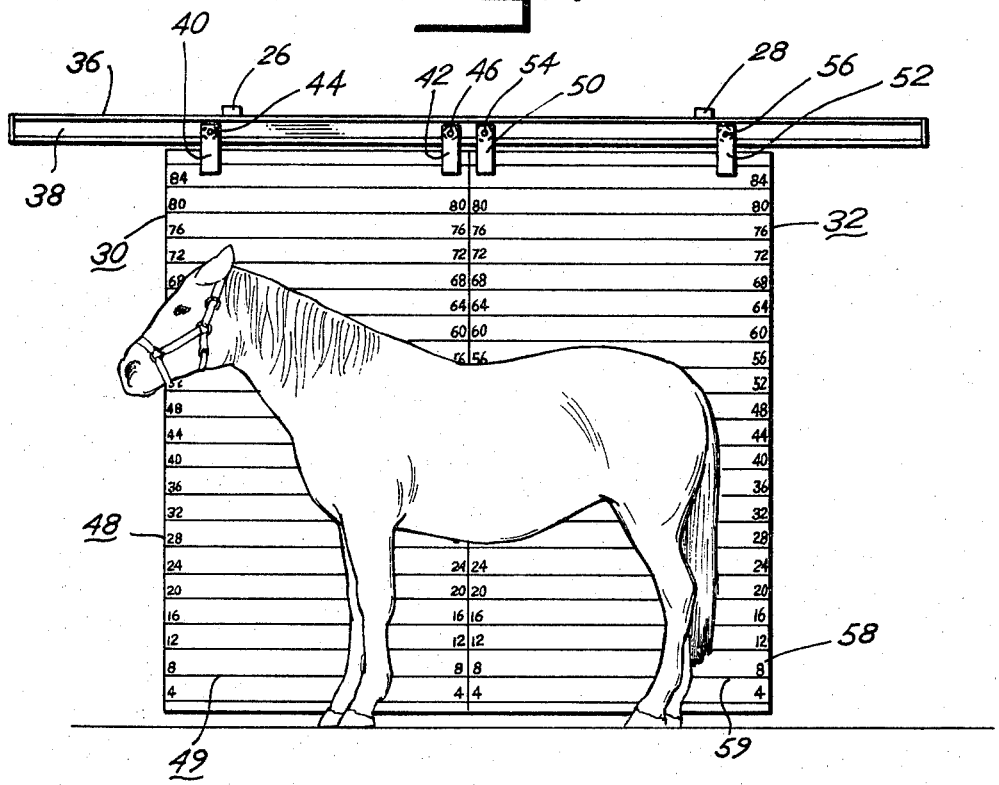
FIG. 1 is an elevational view of an animal measuring apparatus embodying the present invention with a horse properly positioned in front thereof for measuring and/or judging.

Apparatus 10 includes a frame 12 having adjustable wall assemblies 14 and 16 attached thereto. The animals can be positioned in front of or between the wall assemblies while being judged, and the walls provide a consistent background of a suitable color for judging the animals. Frame 12 includes corner posts or upright members 18, 20, 22 and 24 which may be of different heights for different animals; however, to judge horses, cows and the like, the corner posts should be at least about seven to eight feet tall. Cross members 26 and 28 are disposed between corner posts 18 and 20 and 22 and 24, respectively, at or near the top ends thereof. If the apparatus is permanently erected, the corner posts can be embedded in the ground, or the apparatus can be free standing for portable use. Wall assembly 14 includes panels 30 and 32 slidably attached to uprights 18 and 22 by a track mechanism 34. Various types of track mechanisms may be used, and mechanism 34 shown in the drawings includes a track 36 attached to posts 18 and 22 near the top thereof. The track includes a channel 38 and extends outwardly past cross members 26 and 28. Panel 30 includes brackets 40 and 42 which are attached to the panel and extend upwardly therefrom and have rollers 44 and 46 which are disposed in channel 38 and permit the panel to be slid along the track and suspended therefrom. The outer surface of panel 30 is provided with a scale 48 divided into appropriate calibrations for measuring animals. For example, the scale shown in FIG. 1 has four inch markings thereon so that the measurement of a horse can be taken in inches and quickly translated to the often used "hand" measurement, of which one hand equals approximately four inches. Any scale calibration suitable for the animals being judged can be applied to the panel. Preferably the lines 49 of the scale on the panel extend across the full width of the panel so that when the animal stands in front thereof, as shown in FIG. 1, the appropriate line can be cited and read across to the numeral thereof regardless of the exact position of the animal in front of the apparatus.

Brackets 50 and 52 are attached to the top of panel 32 and extend upwardly therefrom and have rollers 54 and 56 disposed in channel 38. A scale 58 having lines 59 is disposed on the outer surface of panel 32 for measuring an animal standing in front thereof, and lines 59 correspond with lines 49 to provide a series of continuous lines across the outer surface presented by the combined panels 30 and 32 when disposed adjacent each other. With the scale disposed across the entire background behind the animal, various measurements of the animal can be taken and compared quickly. For example, the front shoulder height, leg length, hind quarter height and head height can all be taken without moving the animal or scale.

Wall assembly 16 is similar to wall assembly 14 and includes a track 70 having a channel 72 therein from which panels 74 and 76 are suspended. Panel 74 includes brackets 78 and 80 having rollers 82 and 84 disposed in channel 72, and panel 76 includes brackets 86 and 88 having rollers 90 and 92 disposed in channel 72. Side walls can be disposed between the corner posts from wall assembly 14 to wall assembly 16; however, the side walls normally are not required. Bracing members can be disposed between the corner posts and cross members 26 and 28 on larger embodiments to increase the stability and rigidity of the assembly.

In the use and operation of an animal measuring apparatus embodying the present invention, an animal such as a horse is brought to the apparatus and is positioned in front thereof. Panels 30 and 32 are disposed adjacent each other so that the lines of scales 48 and 58 align as shown in FIG. 1. When the animal stands near the panels, a judge positioned some distance away from the animal can quickly ascertain the size of the animal by sighting the nearest line to particular parts of the animal, and following the line across to the numerical designation thereof. For example, the highest point of the horse shown in FIG. 1 at the hind quarters is approximately 60 inches high. This measurement can be compared quickly with front shoulder measurements or the like. Other measurements such as the depth of the chest can also be ascertained quickly by comparing the measurements at the top and bottom of the chest. The depth of the horse's chest shown in FIG. 1 is approximately 28 inches, as the bottom of the horse's belly is approximately 28 inches off the ground, and the top of the back directly thereabove is 56 inches off the ground. The scale also provides reference lines against which the physical features of the animal can be judged. The scale in FIG. 1 indicates that the horse sags approximately four inches from the peak of the hind quarters to a height from the ground near the middle of the horse's back of 56 inches. Similar comparisons can be made between the front shoulders and rear shoulders of the horse to make comparative judgements of the horse with other horses.

Figure 2:
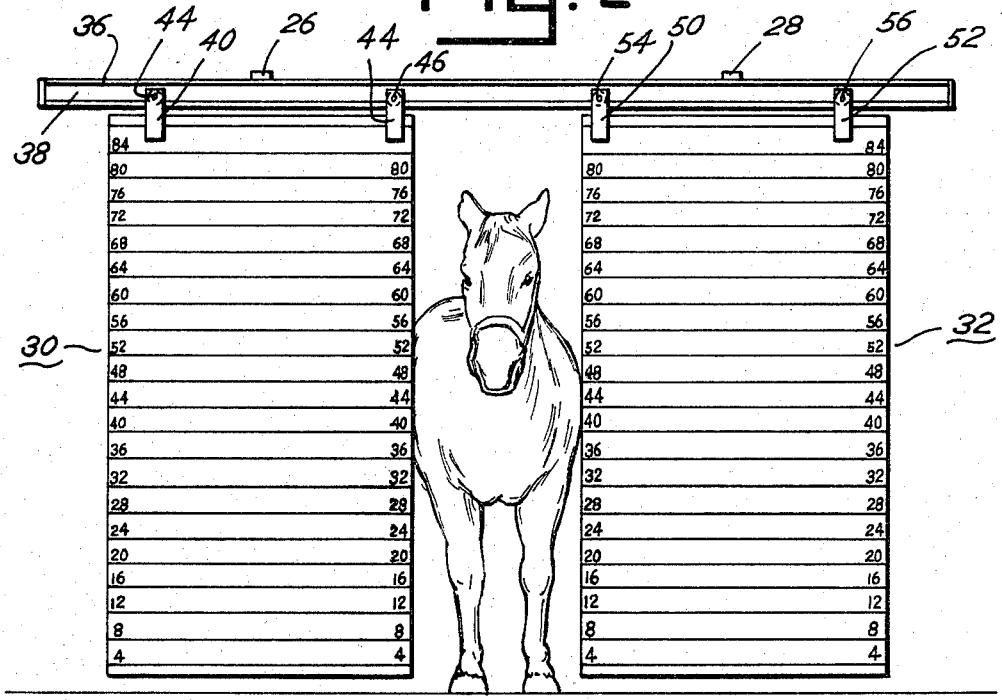
FIG. 2 is an elevational view of the apparatus showing use for assisting in judging the physical characteristics of a horse.

To judge the symmetry of development of the horse, walls 30 and 32 are slid apart, and the horse is positioned therebetween as shown in FIG. 2. The lines and edges of the panels of wall assembly 14 provide references against which the physical characteristics of the horse can be judged, and the panels of wall assembly 16 provide a suitable background for correctly judging whether or not the horse is symmetrically developed. Further, all the panels preferably are colored a dull, light, non-reflective color so that the lines and shape of the horse are readily distinguishable against the light but dull background. The present apparatus can simplify horse judging when compared with situations where the horse is judged against moving backgrounds, excessively bright backgrounds or dark backgrounds which obscure both desirable and undesirable characteristics. A consistent background is provided behind each animal, and the background is nondistractive and enables all animals to be judged on an equal basis.

The present apparatus can be placed at a barn or corral gate so that the animal walks between the panels upon entering the judging arena. Thus panels 30 and 32 would be slid away from each other, and panels 74 and 76 would also be slid away from each other, providing a chute through which the horse may pass. Once the horse is in the judging arena, the walls can be slid together and judging continued as described previously. Since the judges normally will not have to approach the animal being judged, the animal is less likely to be frightened and will remain calm and still, thereby presenting a better and more easily judged posture than when the animal becomes agitated by the approach of judges who are not familiar to the animal. Judges and spectators alike can be positioned away from the animal, and only the animal handler who is known to the animal need be close to the animal to move it into various judging postures. Animal judging tournaments will end with more fair results when the present apparatus is used than when it is not used, in that all animals will be judged against the same background, and precise measurements of the animals as well as more accurate visual appraisals can be made when the apparatus is used.

Although one embodiment of an animal measuring and judging apparatus has been shown and described in detail herein, various changes may be made without departing from the scope of the present invention.

I claim:

1. An animal measuring apparatus comprising a first vertically disposed panel having two vertical sections horizontally moveable relative toward and away from one another, a second vertically disposed panel having two vertical sections horizontally moveable relative to one another and being positioned parallel with and spaced from said first panel, and a measuring scale disposed on at least one of said panels for determining the size and/or physical stature of an animal positioned in front of said last mentioned panel.

2. An animal measuring apparatus as defined in claim 1 in which tracks support said panel sections for said horizontal movement.

3. An animal measuring apparatus comprising a vertically disposed panel having two vertical sections disposed on a substantially common plane and being horizontally moveable on said common plane from a substantially closed position with the facing edges of the two sections in close proximity to one another, to an opened position, to permit the animal being measured to stand in front of or between said sections, a measuring scale disposed on at least one of said sections for determining the size and/or physical stature of the animal positioned in front of or between said sections, a frame means having a support means supported thereby for holding said panels in an upright position with said common plane being in substantially vertical position, and a wall assembly connected to and supported by said frame means and disposed in spaced relation to said panels and providing a background visible through the space between said panels when said panels are disposed apart from each other.

4. An animal measuring apparatus as defined in claim 3 in which said support means include tracks supporting said panel sections for said horizontal movement.

5. An animal measuring apparatus comprising a panel in front of which an animal to be judged can be placed, frame means supporting said panel in a substantially vertical position, a measuring scale disposed on said panel having graduated increments for use in determining the size and physical stature of an animal placed in front of said panel, said panel being slidably connected to said frame means for lateral movement in an upright position, a second panel slidably connected to said frame for lateral movement in a vertical position and having a scale similar to said first mentioned scale connected to said frame, the lines of said scales extending substantially the widths of said panels and being readable from a viewing point spaced forwardly from said panels, and a wall assembly connected to said frame means and disposed in spaced relation to said panels and providing a background visible through the space between said panels when said panels are disposed apart from each other.

6. An animal measuring apparatus as defined in claim 5 in which said panels are of a dull nonreflective color for highlighting the physical characteristics of an animal.

7. An animal measuring apparatus as defined in claim 5 in which said panels and said wall assembly are of a dull nonreflective color for highlighting the physical characteristics of an animal.

8. An animal measuring apparatus as defined in claim 5 in which said wall assembly includes panels slidably attached to said frame means for lateral movement in upright positions.

9. An animal meauring apparatus as defined in claim 5 in which one panel is of a color to highlight the physical characteristics of an animal in front of said panel.

* * * * *